United States Patent
Feinberg

(10) Patent No.: US 9,451,903 B2
(45) Date of Patent: Sep. 27, 2016

(54) SIMULTANEOUS MULTISLICE PERFUSION IMAGING IN MRI

(71) Applicant: David Feinberg, Sebastapol, CA (US)

(72) Inventor: David Feinberg, Sebastapol, CA (US)

(73) Assignee: ADVANCED MRI TECHNOLOGIES, LLC, Sebastopol, CA (US)

( * ) Notice: Subject to any disclaimer, the term of this patent is extended or adjusted under 35 U.S.C. 154(b) by 867 days.

(21) Appl. No.: 13/684,195

(22) Filed: Nov. 22, 2012

(65) Prior Publication Data

US 2013/0204123 A1 Aug. 8, 2013

Related U.S. Application Data

(63) Continuation-in-part of application No. PCT/US2011/057161, filed on Oct. 20, 2011, and a continuation-in-part of application No. 13/632,941, filed on Oct. 1, 2012, which is a continuation of application No. 13/397,634, filed on Feb. 15, 2012, now abandoned.

(60) Provisional application No. 61/394,929, filed on Oct. 20, 2010, provisional application No. 61/443,215, filed on Feb. 15, 2011, provisional application No. 61/444,031, filed on Feb. 17, 2011, provisional application No. 61/444,039, filed on Feb. 17, 2011.

(51) Int. Cl.
| | |
|---|---|
| *G01V 3/00* | (2006.01) |
| *A61B 5/055* | (2006.01) |
| *A61B 5/026* | (2006.01) |
| *G01R 33/483* | (2006.01) |
| *G01R 33/563* | (2006.01) |
| *A61B 5/00* | (2006.01) |
| *G01R 33/561* | (2006.01) |

(52) U.S. Cl.
CPC ............ *A61B 5/055* (2013.01); *A61B 5/0263* (2013.01); *G01R 33/4835* (2013.01); *G01R 33/56366* (2013.01); *A61B 5/0042* (2013.01); *G01R 33/5616* (2013.01)

(58) Field of Classification Search
CPC .................................................. G01R 33/5601
USPC ........................................ 324/306, 307, 309
See application file for complete search history.

(56) References Cited

U.S. PATENT DOCUMENTS

| | | | |
|---|---|---|---|
| 5,327,088 A * | 7/1994 | Pipe .............................. | 324/309 |
| 8,395,385 B2 * | 3/2013 | Lee et al. ...................... | 324/307 |
| 8,791,699 B2 * | 7/2014 | Hernandez-Garcia et al. ............................. | 324/309 |
| 8,941,381 B2 * | 1/2015 | Feinberg et al. ............. | 324/309 |
| 2012/0056620 A1 * | 3/2012 | Feinberg et al. ............. | 324/309 |
| 2012/0319686 A1 * | 12/2012 | Jesmanowicz et al. ...... | 324/309 |
| 2013/0085379 A1 * | 4/2013 | Feinberg ....................... | 600/419 |

* cited by examiner

*Primary Examiner* — Louis Arana
(74) *Attorney, Agent, or Firm* — Cooper & Dunham LLP

(57) ABSTRACT

An MRI system and method for dynamic susceptibility contrast (DSC) imaging use multiplexed echo planar imaging (M-EPI) to essentially simultaneously acquire MR signals for perfusion parameter images of multiple slices. This essentially simultaneous acquisition of MR signals for multiple slices can be repeated in rapid succession without deteriorating T2* contrast, which makes it practical to image multiple perfusion phases and brings about other significant benefits.

12 Claims, 3 Drawing Sheets

SIMULTANEOUS MULTISLICE PERFUSION IMAGING IN MRI

CROSS-REFERENCE TO RELATED APPLICATIONS AND INCORPORATION BY REFERENCE

This patent application is a continuation-in-part of (a) PCT International Application No. PCT/US11/57161, filed Oct. 20, 2011, which claims the benefit of U.S. Provisional Application No. 61/394,929, filed Oct. 20, 2010, and (b) U.S. patent application Ser. No. 13/632,941, filed Oct. 1, 2012, which is a continuation of U.S. patent application Ser. No. 13/397,634, filed Feb. 15, 2012, which claims the benefit of U.S. Provisional Application Nos. 61/443,215, filed Feb. 15, 2011, 61/444,031, filed Feb. 17, 2011, and 61/444,039, filed Feb. 17, 2011. This patent specification incorporates by reference the entire contents of each of these applications, including their drawings and the appendices attached thereto.

FIELD

This patent specification is in the field of magnetic resonance imaging (MRI). More specifically it pertains to simultaneously imaging tissue perfusion in multiple slices without a need for arterial spin labeling.

BACKGROUND AND SUMMARY OF THE DISCLOSURE

One method of imaging perfusion in living tissue involves arterial spin labeling (ASL) using echo planar imaging (EPI). Following a blood labeling pulse, a train of MR signals is acquired in a sequence of read periods and an MR image of the slice is reconstructed. This can be repeated to produce additional perfusion images of the slice that show later perfusion phases. Significant improvements, described in other patent applications of the inventor named in this patent application, also use ASL but replace the conventional EPI imaging with multiplexed EPI and/or simultaneous image refocusing (SIR) to speed up image acquisition and provide other benefits.

A common method of imaging with dynamic contrast enhancement involves the introduction of a contrast agent into a patient's vasculature and generating contrast-enhanced dynamic images that emphasize blood vessels in which the agent is present by shortening the T1 relaxation of blood to increase ("enhance") the signal. Typically, a gadolinium-based contrast agent is injected in an artery and the agent moves through the artery and capillaries that it feeds and then into the venous system. At selected times before (baseline), during and after the injection, MRI images of one or more slices are taken. 2D EPI pulse sequences typically are used to generate slice images. The images make use of the decrease in signal intensity from T2 and T2* relaxation times that depend on the local concentration of the agent.

A new approach described in this patent specification involves also using a contrast agent that decreases signal intensity by T2 and T2* relaxation but utilizes a different way to acquire the MR signals that brings about significant practical advantages. In particular, the new approach improves perfusion imaging by carrying out dynamic susceptibility contrast (DSC) MRI perfusion imaging using multiplexed EPI that rapidly and essentially simultaneously acquires MR signals for multiple slices, using a fast TR or the shortest possible time intervals. In DSC-MRI using the new acquisition, which can be called M-EPI acquisition, a gadolinium-based contrast agent is injected and a time series of sets of fast T2*-weighted images is acquired in timed relationship to the injection. Each set is acquired essentially simultaneously and comprises MR signals for multiple slices, e.g., between 2 and 100 slices. As gadolinium passes through the tissues, it produces a reduction of T2* intensity depending on local concentration. The acquired MR signals are then post-processed to obtain perfusion maps with different parameters, such as BV (blood volume), BF (blood flow), MTT (mean transit time) and TTP (time to peak). Here the M-EPI acquisition sequence is defined as a simultaneous image acquisition sequence that can use simultaneous image refocusing (SIR) or multiband (MB) radio frequency (RF) excitation pulses or both SIR and MB within the same MR signal acquisition sequence. Therefore the M number of simultaneously acquired slices causing a reduction in TR and scan time can be defined as M=MB if only MB is utilized, M=SIR if only SIR is used or M=SIR×MB when both SIR and MB are used in the imaging sequence. For example when MB=5 then the scan time is reduced by a factor of 5 and the minimum TR can be reduced accordingly.

One result of the new approach, which may have appeared counterintuitive in the field of conventional MRI perfusion imaging, is that a volume of a patient's body may be more rapidly imaged with the T2* contrast inherent in the M-EPI. Previously known techniques of faster conventional EPI imaging may have used shorter echo train lengths and earlier TEs to reduce the time of each slice, but both reduce the T2* contrast in the image. Therefore, such earlier methods required changing or reducing TE and echo train length and dependent T2* contrast needed for DSC imaging. The known prior work did not appear to appreciate that M-EPI without a need for ASL can achieve several times faster imaging by simultaneity of 2D slices without requiring shorter echo trains or TE parameters that would reduce T2* contrast when using conventional EPI MR signal acquisition.

Another benefit of the new approach is that it can achieve more rapid sampling of a contrast bolus. With the new DSC M-EPI process not reducing T2* contrast sensitivity to the contrast agent, DSC perfusion imaging can be improved by using M-EPI to achieve a shorter TR, for many more measurements of T2* dependent signal intensity during the passage of a bolus of contrast agent. The resulting increased number of MR time-signal points can greatly improve the statistics and therefore the precision in the measurements of time-signal intensity curves used to calculate perfusion and other physiological parameters including mean transit time and blood volume changes.

Yet another benefit of the DSC M-EPI described in this patent specification is that with its greater speed providing more measurements of contrast passage dependent signal change, it is possible to use a lower dosage of contrast agents, reducing the risk of kidney function deterioration in patients who are susceptible to this problem at higher dosages of contrast agent.

Still another improvement when utilizing the new kind of DSC M-EPI process is that the arterial input function can be measured simultaneously with acquiring the perfusion data so that two bolus injections of contrast agent are not necessary and there is improved quantitation in deconvolving the input function given its identical physiological conditions achieved through simultaneity of measurements. For example, one or more of the several simultaneously acquired MR images can be for a slice or slices positioned over an artery feeding the tissue in which perfusion MR images are being acquired using the new process so that the arterial input function is acquired with the same hemodynamics of the perfused tissue. This MR image measuring the arterial input function may be positioned outside of the perfusion region where a feeding vessel lies. The arterial input function also can be measured in a separate MR data acquisition or within an artery included in the images of the perfused tissue, such as the aorta included in renal perfusion images, or cerebral arteries included in images of the brain. The new ability to position an EPI image on a blood vessel of interest during the new kind of DSC acquisition can improve calculations of perfusion, MTT, BF and BV by orienting the image to reduce partial volume errors and/or by having advantages in more direct timing correlations with the perfusion in a particular organ.

To obtain the T2* sensitivity desired for the new kind of DSC, it is possible to very rapidly acquire multiplexed EPI during the passage of an exogenous contrast agent injected into the vasculature. M-EPI combined with IV injected contrast agents takes advantage of the inherent T2* contrast of the M-EPI image and can show well a decreased signal during the passage of contrast agents through imaged body regions. Using the inherent T2* contrast of M-EPI in subjects who can undergo this procedure, it can be unnecessary to use of ASL labeling pulses to make perfusion images of the body. In the new approach, the contrast agent can be, and preferably is, injected rapidly, which can further improve the pertinent calculations of perfusion parameters.

The perfusion maps constructed from the new kind of dynamic susceptibility perfusion MR images using M-EPI can be based on the change in MR signal intensity (S) observed during the passage of contrast material relative to a baseline (S0). Subsequently, these measurements can be converted to a change in T2* relaxation rate, such as by using the formula:

$$-\ln [S/S0]/TE$$

Changes in T2* relaxation rate can be considered to be linearly proportional to the concentration of contrast material in tissue, which allows the time-signal-intensity curve to be converted to a time-concentration curve. This calculation allows hemodynamic parameters to be generated on a voxel-by-voxel basis.

DETAILED DESCRIPTION OF PREFERRED EMBODIMENTS

Figure 1:
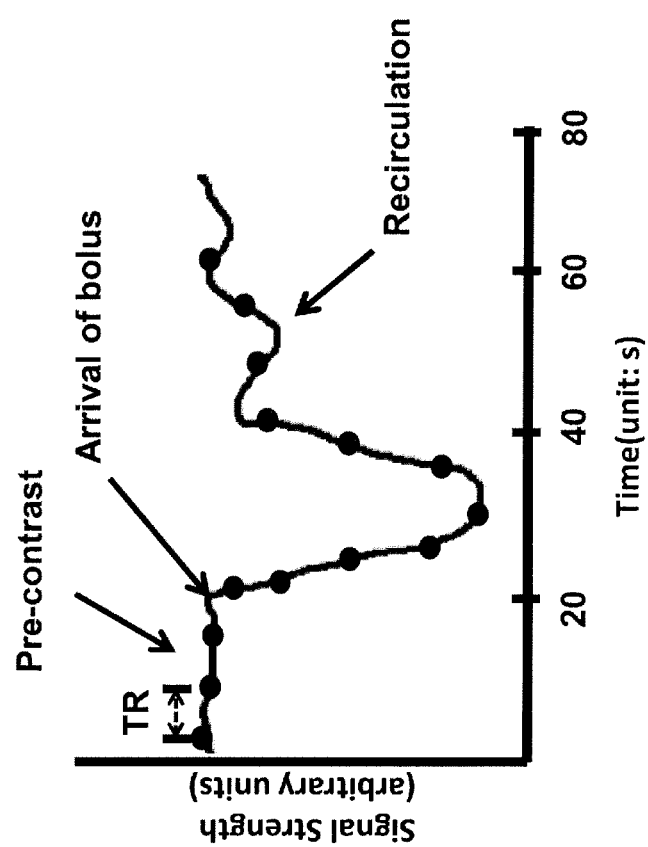
FIG. 1 illustrates a multi-slice EPI imaging process.
Figure 2:
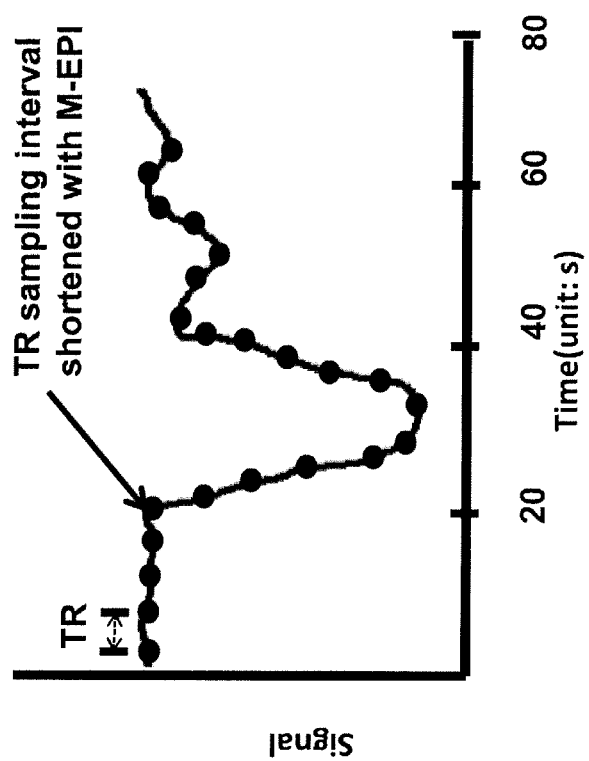
FIG. 2 illustrates a new process with shortened TR sampling rate using M-EPI.
Figure 3:
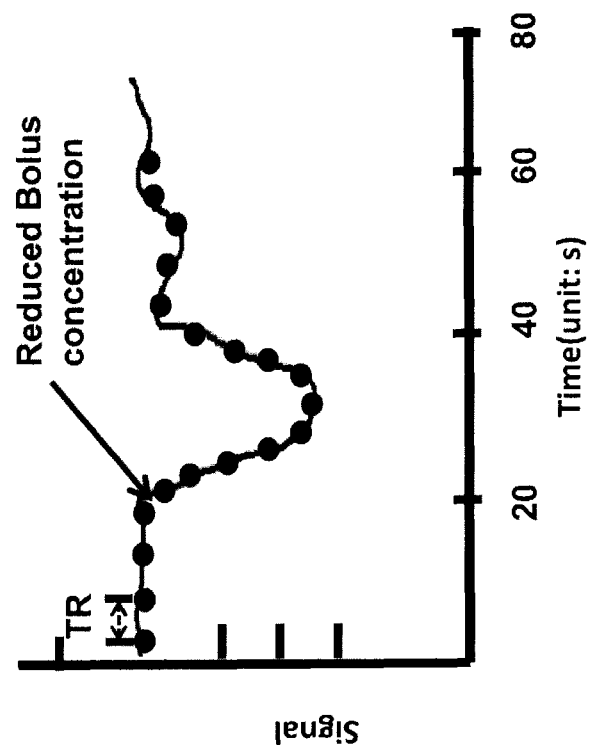
FIG. 3 illustrates the use of lower concentration of a contrast agent in the new process

FIGS. 1-3 illustrate graphs of MR signal strength in arbitrary MR units within the brain tissue or other body organ plotted against time, from Pre-contrast injection period to bolus arrival time and subsequent signal intensity. The curves show a drop in MR signal strength in the tissue followed by recirculation of the contrast agent causing a smaller secondary drop.

FIG. 1 shows a curve using multi-slice EPI in which TR sampling rate is shown as vertical hatch marks on the curve.

FIG. 2 shows the higher sampling of the dynamic contrast signal curve using the shortened TR using M-EPI according to the new method of this patent specification. The curve is more highly sampled to give greater accuracy in model fitting to determine perfusion and bolus transit time in each image voxel.

FIG. 3 shows the use of a lower concentration of contrast agent where the greater sampling of M-EPI gives better definition of the curve than possible using a sparser sampling with slower TR of EPI as in prior methods.

The new process discussed above can be implemented in a conventional MRI system by using therein pulse sequence techniques that are individually described in the patent applications incorporated by reference in this patent specification but are adapted to carry out the M-EPI process with the use of a contrast agent bolus. The necessary pulse sequence can be programmed according to the descriptions in the patent specification and in the patent applications and literature (cited below) and incorporated by reference in this patent specification without undue experimentation or additional inventive skills. The resulting program can be stored in computer-readable media such as optical or hard discs, for loading into an MRI system as a new pulse sequence. The MRI system with such program loaded in it and capable of running in it then becomes a new system. As noted, the multiplexing in M-EPI can be multiplexing in time or multiplexing in frequency (multiband pulses).

An explanation and illustrations of M-EPI and SIR pulse sequences, and MRI scanners using them, can be found in the PCT application and the U.S. application that are incorporated by reference in this patent specification. In addition, the following papers may provide useful background and are hereby incorporated by reference:

1. Barbier E L, et al., Perfusion Imaging Using Dynamic Arterial Spin Labeling (DASL), Magnetic Resonance in Medicine 45:1021-1021 (2001);
2. Wang Y, Regional reproducibility of pulsed arterial spin labeling perfusion imaging at 3T, NeuroImage 54 (2011) 1188-1195;
3. Wang J, Reduced susceptibility effects in perfusion fMRI with single-shot spin-echo EPI acquisitions at 1.4 Tesla, Magnetic Resonance Imaging 22 (2004) 1-7; and
4. Donahue M J, et al., Cerebral blood flow, blood volume, and oxygen metabolism dynamics in human visual and motor cortex as measured by whole-brain multi-modal magnetic resonance imaging, Journal of Cerebral Blood Flow & Metabolism (2009) 29, 1856-1866.

What is claimed is:

1. A magnetic resonance (MR) method of dynamic susceptibility contrast (DSC) perfusion imaging using multiplexed echo planar imaging (M-EPI) to simultaneously image a set of multiple slices and rapidly repeat the imaging of the set of slices in timed relationship to an introduction of contrast agent, comprising:
    (a) positioning a patient in a magnetic resonance imaging (MRI) scanner;
    (b) introducing an MRI contrast agent into the patient's vascular system;
    (c) applying a radiofrequency (RF) excitation pulse multiplexed in time or frequency to the patient in a selected time relationship to the introduction of the contrast agent;
    (d) essentially simultaneously acquiring MR signals for multiple slices of the patient generated in response to the RF excitation pulse, using EPI signal acquisition;
    (e) repeating steps (c) and (d) at least once, each repetition being in a selected time relationship to the introduction of the contrast agent, using shorter time intervals TR between repetitions compared with conventional EPI imaging; and (f) computer-processing the MR signals to derive images of perfusion parameters for the patient's anatomy related to at least some of said slices.

2. The method of claim 1 in which step (e) comprises repeating steps (c) and (d) at least 10 times.

3. The method of claim 1 in which step (e) comprises repeating steps (c) and (d) at least 50 times.

4. The method of claim 1 in which said TR is ≤2000 msec.

5. The method of claim 1 in which step (d) comprises acquiring the MR signals for all of the multiple slices in a read period TE≤100 msec.

6. The method of claim 1 in which step (f) comprises relating the MR signals S(0) acquired in response to one of the RF excitation signals to respective MR signals S acquired in response to other RF excitation pulses to derive perfusion images or metrics related to changes in T2* relaxation time using a formula $$-\ln(S/S0)/TE$$

where TE is related to a time period for essentially simultaneously acquiring the MR signals for the multiple slices generated in response to a multiband RF excitation pulse.

7. The method of claim 1 in which at least one of the multiple slices for which MR signals are acquired essentially simultaneously is at a location in the patient's body related to an arterial input and at least one other slice is at a location for which perfusion metrics related to flow from the input.

8. The method of claim 1 in which step (d) is repeated multiple times in respective time intervals related to perfusion before, during and after the contrast agent is introduced.

9. The method of claim 1 in which the RF excitation pulse is a multiband pulse multiplexed in frequency.

10. The method of claim 1 in which the FR excitation pulse is multiplexed in time and comprises a sequence of pulses closely spaced in time.

11. The method of claim 1 in which the step of introducing a contrast agent into the patient's vascular system comprises introducing a lower dose than in conventional dynamic susceptibility contrast (DSC) MRI perfusion imaging.

12. A system comprising:
an MRI data acquisition unit configured for imaging a patient;
a contrast agent injection system configured to introduce an MRI contrast agent into the vascular system of a patient being imaged with said MRI data acquisition unit;
a computer coupled with the MRI data acquisition unit and configured to cause the unit to apply a radiofrequency (RF) excitation pulse multiplexed in time or frequency to the patient in a selected time relationship to the introduction of the contrast agent;
said computer being further configured to cause the data acquisition unit to essentially simultaneously acquire MR signals for multiple slices of the patient generated in response to the RF excitation pulse, using EPI signal acquisition, and to repeat the application of the RF pulse and the acquisition of MR signals plural times, each repetition being in a selected time relationship to the introduction of the contrast agent, using shorter time intervals TR between repetitions compared with conventional EPI imaging; and
said computer being further configured to process the MR signals to derive images of perfusion parameters for the patient's anatomy related to at least some of said slices.

* * * * *